US011235088B1

United States Patent
Provonchee et al.

(10) Patent No.: US 11,235,088 B1
(45) Date of Patent: Feb. 1, 2022

(54) LOW MELT TEMPERATURE AGAROSE FOR DERMAL FILLING AND RELATED APPLICATIONS AND METHODS

(71) Applicant: Advanced Aesthetic Technologies, Inc., Brookline, MA (US)

(72) Inventors: Richard Provonchee, Cushing, ME (US); Leonard Miller, Chestnut Hill, MA (US)

(73) Assignee: ADVANCED AESTHETIC TECHNOLOGIES, INC., Brookline, MA (US)

( * ) Notice: Subject to any disclaimer, the term of this patent is extended or adjusted under 35 U.S.C. 154(b) by 190 days.

(21) Appl. No.: 16/403,905

(22) Filed: May 6, 2019

Related U.S. Application Data

(60) Provisional application No. 62/666,877, filed on May 4, 2018.

(51) Int. Cl.
*A61L 27/20* (2006.01)

(52) U.S. Cl.
CPC ........... *A61L 27/20* (2013.01); *A61L 2400/06* (2013.01); *A61L 2430/34* (2013.01)

(58) Field of Classification Search
CPC .. C08B 37/0039; A61L 27/20; A61L 2400/06; A61L 2430/34
See application file for complete search history.

(56) References Cited

U.S. PATENT DOCUMENTS

2012/0078229 A1\* 3/2012 Emans ................ A61L 27/3852
604/522

OTHER PUBLICATIONS

Agarose (Low-Melting, Nucleic Acid Recovery/Molecular Biology Grade), Fisher Scientific; available at https://www.fishersci.com/shop/products/agarose-low-melting-nucleic-acid-recovery-molecular-biology-grade-fisher-bioreagents/BP16525; obtained online Jan. 6, 2020. (Year: 2020).\*
Zarrintaj, P. et al., Carbohydrate Polymers, "Agarose-based biomaterials for tissue engineering", Jan. 2018, vol. 187, pp. 66-84 (Year: 2018).\*
Lemperle, G. et al., Plastic and Reconstructive Surgery, "A Classification of Facial Wrinkles", 2001, vol. 108, pp. 1735-1750 (Year: 2001).\*
Mak, W.C. et al., J. Funct. Biomater., "Controlled Delivery of Human Cells by Temperature Responsive Microcapsules", 2015, vol. 6, pp. 439-453 (Year: 2015).\*
Scarano, A. et al., Oral Surg Oral Med Oral Pathol Oral Radiol Endod, "Lip augmentation with a new filler (agarose gel): a 3-year follow-up study", 2009, vol. 108, pp. e11-e15 (Year: 2009).\*

\* cited by examiner

*Primary Examiner* — Bahar Craigo
(74) *Attorney, Agent, or Firm* — Hayes Soloway PC

(57) ABSTRACT

Dermal filling materials and techniques are disclosed herein. In particular, dermal fillers containing low melt agarose (i.e., agarose having a melting temperature of less than 65° C.) are described. The disclosed dermal fillers can be manipulated after injection by, for example, heating and/or cooling the dermal filler while inside the patient to adjust its positioning or stiffness.

5 Claims, No Drawings

LOW MELT TEMPERATURE AGAROSE FOR DERMAL FILLING AND RELATED APPLICATIONS AND METHODS

CROSS REFERENCE TO RELATED APPLICATION

This application claims priority from U.S. Provisional Application Ser. No. 62/666,877, titled "Low Melt Temperature Agarose for Dermal Filling and Related Applications and Methods" filed May 4, 2018, the contents of which is incorporated by reference herein.

BACKGROUND

Agarose is a linear polysaccharide polymer made up of repeating units of agarobiose, which is a disaccharide formed of D-galactose and 3,6-anhydro-L-galactopyranose. Agarose is one of the two principal components of agar and is purified from agar by removing agar's other component, agaropectin. Agarose is frequently used in molecular biology for the separation of large molecules, especially DNA, by electrophoresis.

SUMMARY

This disclosure relates to the use of low melting temperature agaroses for dermal filling and other related applications. The use of these agaroses can, in some cases, provide for the reversal, or at least reduction of, the appearance of a dermal fill. Additionally, the disclosed low melt temperature agarose may allow for an area of dermal or subcutaneous augmentation to be adjusted after application by, for example, using heating and/or cooling techniques. These agaroses may also be degraded by select enzymes in situ.

Conventional agarose has a melting temperature above about 80° C., whereas many low melt agaroses have melting temperatures below 60° C. and some can have melt temperatures below 50° C. These "low melt" agaroses, as referred to herein, also tend to have low gel strength compared to conventional agaroses. As described in detail below, low melt agaroses may be well-suited for use in dermal filling applications (e.g., materials injected into the body to mimic the effect of soft tissue).

One of the shortcomings of using conventional agarose (having a melting point above 80° C.) for dermal filling is the lack of a convenient method to reverse the procedure. That is, there is no 'undo' button once the dermal filler has been administered. Although there are enzymes that will eventually degrade agarose, these enzymes act slowly and generally require the agarose to be in melted (as opposed to gelled) form.

SUMMARY

Using low melt agarose in dermal filling applications can provide an opportunity to easily reverse, or at the very least reduce the effect of, the dermal filling procedure, which has been heretofore unavailable. The phrase 'dermal filling procedure' as used herein, refers to any procedure in which an injectable dermal filler is administered to a patient. Dermal filling procedures may be used for any of the following cosmetic or medical purposes: filling in wrinkles, fine lines, or deep creases, improving skin imperfections, such as scars, adding volume to lips or cheeks, contouring the jaw line, or adjusting the appearance of any other body part, such as rhinoplasty. The disclosed methods may be especially useful in procedures in which an agarose filling material is administered within 20 mm, 15 mm, 10 mm, or 5 mm of the skin's surface and at any level at a depth of up to 2 mm from the dermal layer.

DETAILED DESCRIPTION

Example low melt agaroses that may be used in connection with the disclosed methods include agarose having a melting point of less than 65° C. In some embodiments, the low melt agarose used in the disclosed methods has a melting point of below 60° C., 55° C., 50° C., 45° C., or 40° C. An example low melt agarose that may be used in the disclosed methods is SeaPrep agarose (Lonza Rockland), which has a melt temperature of less than 51° C. However, any other agarose having a melting temperature within the disclosed ranges may also be used.

In some example embodiments, a dermal filling procedure is performed in which a low melt agarose is injected into a patient. Any time after injection (for example, within 24 hours, 48 hours, 72 hours, or longer) the injected filler may be adjusted using any of the described techniques. In some example embodiments in which alteration or reversal of the filling procedure is desired, heat may be applied to the skin above the injected filler. Any suitable method of heating the dermal and/or subdermal areas of the skin may be used (e.g., applying infrared and/or radio frequency radiation to the skin). In some example embodiments, a Thermi® radio frequency heating electrode device may be used to heat the dermal filler. In some embodiments, the injected agarose filler may be heated for at least 15 seconds, 30 seconds, 45 seconds, 1 minute, 5 minutes, 10 minutes, 20 minutes, 30 minutes, or longer.

Using the selected heating technique, the injected dermal filler may be brought near or above its melting temperature. After or as the injected agarose-based filler melts, the dermal filler may be adjusted (for example, by massaging or otherwise re-shaping the filler) to a more desirable location and/or shape. Also, if desired, the agarose filler may be only partially heated such that only a targeted portion of the filler melts, thereby allow a partial modification or reshaping of the filler.

Because agarose has a significant hysteresis between melting and gelling temperatures, the agarose may not re-gel as the area returns to body temperature. For example, SeaPrep agarose will not gel until the temperature drops below 17° C. Therefore, if it is desired to have the agarose re-gel, the area can be chilled, for instance, with an ice pack or other cooling mechanism. The hysteresis between melting and gelling temperatures in agaroses can be used to provide many interesting possibilities.

For example, in some cases, the agarose filler may be heated/dissolved incrementally rather than in a single procedure. Because the dissolved agarose will not re-gel without exposure to its gelling temperature (generally quite below body temperature), these heating/dissolving cycles can take place over an extended time period—e.g., hours, days, weeks, or longer. Incremental heating techniques may be especially advantageous if the agarose filler cannot easily, comfortably, or safely be melted in one heating cycle. That is, the site may be heated for short period of time allowing some of the agarose to melt, then the site could be allowed to cool and recover before heating again to dissolve more of the agarose.

There may be circumstances in which it is advantageous to have the agarose dermal filler in the form of a cohesive gel rather than gel particles. In some such cases, the gel particle agarose dermal filler may be melted in-situ by heating the site and then gelled by applying cold to the site. It may also prove advantageous to hold the melted agarose in a desired shape during the gelling step.

Over time, the body breaks down the injected agarose and the effects of the dermal filler lessen and can eventually vanish. Agarose is generally injected in its gelled form and lasts for a relatively long time before being broken down by the body. Melting or dissolving the agarose in the body may allow for faster breakdown of the agarose. Accordingly, if a patient wishes to quickly reverse the effects of a dermal filling procedure, melting/dissolving the agarose filler using heat may allow for quicker dissipation and full or partial reversal of the procedure.

In these and other embodiments, one or more enzymes may also be injected into the patient to partially or fully reverse the effects of a dermal filling procedure. While enzymes that degrade agarose are known, these enzymes either do not attack agarose in its gelled state or function very poorly to degrade agarose in its gelled state. However, enzymes may be introduced to the patient after the agarose filler has been melted to attack and degrade the agarose filler present if reversal of the procedure or removal of the filler is desired. Example enzymes that may be used to degrade agarose filler include but are not limited to: agarose 4-glycanohydrolase, and hyaluronidase. By using a low melt agarose in the dermal filler, melting/dissolving the agarose within the body, and introducing one or more enzymes to degrade the agarose, it is possible to more quickly dissipate the agarose than it would naturally degrade and dissipate within the body in its gelled form.

What is claimed is:

1. A method for performing dermal filling procedures comprising: injecting a low melting temperature agarose into a patient's skin at any level at a depth of up to 2 mm from a dermal layer, wherein the low melting temperature agarose has a melting temperature below 60° C.

2. The method of claim 1, wherein the dermal filling procedures comprise one or more of: filling in wrinkles, fine lines, or deep creases, adding volume to lips or cheeks, contouring the jaw line, and combinations thereof.

3. The method of claim 1, wherein the low melting temperature agarose has a melting temperature below 51° C.

4. A method for performing dermal filing procedures comprising:
  injecting a low melting temperature agarose into a patient's skin at any level at a depth of up to 2 mm from the dermal layer, wherein the low melting temperature agarose has a melting temperature below 65° C.; and
  heating the dermal and/or subdermal areas of the patient's skin to alter or reverse the filling procedure.

5. The method of claim 4, further comprising injecting agarose 4-glycanohydrolase, hyaluronidase or combination thereof into the patient's skin to degrade heated agarose.

* * * * *